(12) United States Patent
Allais et al.

(10) Patent No.: US 10,183,923 B2
(45) Date of Patent: Jan. 22, 2019

(54) METHOD FOR SYNTHESIZING A PRECURSOR OF A SINGLE DAIRY-LACTONE ISOMER

(71) Applicants: INSTITUT DES SCIENCES ET INDUSTRIES DU VIVANT ET DE L'ENVIRONNEMENT—AGROPARIS TECH, Paris (FR); UNIVERSITY OF NEW ENGLAND, New South Wales (AU); CIRCA GROUP PTY LTD, Coburg North, Victoria (AU)

(72) Inventors: Florent Allais, Bouy (FR); Amandine Flourat, Reims (FR); Aurélien Peru, Reims (FR); Ben Greatrex, Black Mountain (AU); Warwick Raverty, Viewbank (AU); Anthony Duncan, Brighton (AU)

(73) Assignees: INSTITUT DES SCIENCES ET INDUSTRIES DU VIVANT ET DE L'ENVIRONNEMENT—AGROPARIS TECH, Paris (FR); UNIVERSITY OF NEW ENGLAND, Armidale, New South Wales (AU); CIRCA GROUP PTY LTD, Coburg North, Victoria (AU)

(*) Notice: Subject to any disclaimer, the term of this patent is extended or adjusted under 35 U.S.C. 154(b) by 0 days.

(21) Appl. No.: 15/565,287

(22) PCT Filed: Apr. 8, 2016

(86) PCT No.: PCT/FR2016/050813
§ 371 (c)(1),
(2) Date: Oct. 9, 2017

(87) PCT Pub. No.: WO2016/162646
PCT Pub. Date: Oct. 13, 2016

(65) Prior Publication Data
US 2018/0072693 A1    Mar. 15, 2018

(30) Foreign Application Priority Data

Apr. 10, 2015   (FR) .................................. 15 53112

(51) Int. Cl.
C07D 307/02    (2006.01)
C07D 307/33    (2006.01)
(Continued)

(52) U.S. Cl.
CPC .......... C07D 307/33 (2013.01); A23L 27/205 (2016.08); C07C 67/343 (2013.01);
(Continued)

(58) Field of Classification Search
CPC ..... C07D 307/33; C07D 303/40; C12P 17/06; A23L 27/205; C07C 67/343;
(Continued)

(56) References Cited

FOREIGN PATENT DOCUMENTS

EP    0578388 A2    1/1994
FR    1453957       7/1966

OTHER PUBLICATIONS

Fang et al, Asymmetric Transfer Hydrogenation of Functionalized Acetylenic Ketones, Journal of Organic Chemistry, 2013, 78(17), p. 8594-8605. (Year: 2013).*

(Continued)

*Primary Examiner* — Taylor V Oh
(74) *Attorney, Agent, or Firm* — TraskBritt, P.C.

(57) ABSTRACT

This disclosure provides a method for preparing a precursor of a single dairy-lactone isomer, methods of preparing a single dairy-lactone isomer, and to the organoleptic uses thereof.

15 Claims, 3 Drawing Sheets

(51) Int. Cl.
| | |
|---|---|
| *C07D 303/40* | (2006.01) |
| *C07C 67/343* | (2006.01) |
| *C12P 17/06* | (2006.01) |
| *A23L 27/20* | (2016.01) |
| *B01J 23/44* | (2006.01) |
| *G01J 4/00* | (2006.01) |
| *G01R 33/46* | (2006.01) |

(52) U.S. Cl.
CPC ............ *C07D 303/40* (2013.01); *C12P 17/06* (2013.01); *A23V 2002/00* (2013.01); *A23V 2200/15* (2013.01); *B01J 23/44* (2013.01); *C07B 2200/07* (2013.01); *G01J 4/00* (2013.01); *G01R 33/46* (2013.01)

(58) Field of Classification Search
CPC .. C07B 2200/07; B01J 23/44; A23V 2200/15; A23V 2002/00; G01R 33/46
USPC ........................................................ 549/295
See application file for complete search history.

(56) References Cited

OTHER PUBLICATIONS

Begemann et al., The Synthesis of Lactones. Part III: [delta]-Enollactones and Lactones with Exocyclic Double Bonds, REcuel des Travaux Chimiques des Pays-Bas, vol. 86, Issue 12, (Sep. 2, 1967), pp. 1335-1344.

Frerot et al: Easy Access to Aroma Active Unsaturated [gamma]-Lactones by Addition of Modified Titanium Homoenolate to Aldehydes, Journal of Agricultural and Food Chemistry, vol. 59, No. 8, Apr. 27, 2011 (Apr. 27, 2011), pp. 4057-4061.

Habel et al., Efficient and Flexible Synthesis of Chiral [gamma]- and [delta]-lactones, Organic & Biomolecular Chemistry, vol. 6, No. 9, (2008), pp. 1601-1602.

Habel et al: "Efficient and flexible Synthesis of Chiral [gamma]-and [delta]-Lactones Supporting Information", Efficient and Flexible Synthesis of Chiral [Gamma]- and [Delta]-Lactones (Supporting Information), (Mar. 10, 2008), XP055215230.<URL:http://www.rsc.org/suppdata/ob/b8/b801514g/b801514g.pdf,.

Heiba et al., Oxidation by metal salts. X. One-step synthesis of .gamma.-lactones from olefins, Journal of the American Chemical Society, vol. 96, No. 26, (1974), pp. 7977-7981.

International Search Report for International Application No. PCT/FR2016/050813 dated Jul. 18, 2016, 4 pages.

International Written Opinion for International Application No. PCT/FR2016/050813 dated Jul. 18, 2016, 8 pages.

Midland et al: The synthesis of naturally occurring 4-alkyl- and 4-alkenyl-[gamma]-lactones using the asymmetric reducing agent -3-pinanyl-9-borabicyclo[3.3.1]nonane, Tetrahedron Letters, vol. 21, No. 37, (1980), pp. 3549-3552.

Stuart et al: Cobalt-mediated Alkylation of Siloxy Furans, Heterocycles : An International Journal for Reviews and Communications in Heterocyclic Chemistry , Japan Institute of Herocyclic Chemistry, vol. 32, No. 5, (1991), pp. 949-963 (abstract only).

Trygstad et al: Versatile Synthesis of the C3-C14 Domain of 7-Deoxyokadaic Acid, The Journal of Organic Chemistry, vol. 74, No. 2, (Jan. 16, 2009), pp. 910-913.

* cited by examiner

METHOD FOR SYNTHESIZING A PRECURSOR OF A SINGLE DAIRY-LACTONE ISOMER

CROSS-REFERENCE TO RELATED APPLICATIONS

This application is a national phase entry under 35 U.S.C. § 371 of International Patent Application PCT/FR2016/050813, filed Apr. 8, 2016, designating the United States of America and published as International Patent Publication WO 2016/162646 A1 on Oct. 13, 2016, which claims the benefit under Article 8 of the Patent Cooperation Treaty to French Patent Application Serial No. 1553112 filed Apr. 10, 2015.

TECHNICAL FIELD

This application is in the field of aromatic molecules, their manufacturing method and use.

More particularly, the present application provides a synthesis method of dairy-lactone and various precursors for their use for their organoleptic properties in the food industry, pharmaceutics, cosmetics and perfumeries.

BACKGROUND

Known from the prior art is a synthesis method of the dairy-lactone by fermentation.

Patent EP0578388 describes a fermentation method for preparing 10-hydroxy-C18-carboxylic acid derivatives and compositions comprised therefrom and compositions comprising derivatives of gamma-dodecalactone (including dairy-lactone) for their uses for their organoleptic properties, in particular, to increase or correct the aroma of perfumes or fragrances, perfumed articles, food products, chewing gum, toothpaste, hair products, and tobacco. Gamma-lactones are useful as food flavors (Eric Frerot et al., "Easy access to active aroma unsaturated (gamma)-lactones by addition of modified titanium homoenolate to aldehydes," *Journal of Agricultural and Food Chemistry*, 2011).

Also known from the prior art is the dairy-lactone and its enantiomers (Andreas Habel et al., "Efficient and flexible synthesis of chiral (gamma)- and (delta)-lactones," *Organic and Biomolecular Chemistry*, 2008; Mark Midland et al., "the synthesis of naturally occurring 4-alkyl and -4-alkenyl-(gamma)-lactones using asymmetric reducing agent-3-pinanyl-9-borabicyclo(3.3.1)nonane," *Tetrahedron Letters*, 1980).

Finally, also known from the prior art are synthesis methods of different intermediates that can be involved in the synthesis of lactones (P. Haverkamp Begemann et al., "the synthesis of lactones Part III: (delta)-enollactones and lactones with exocyclic double bonds," Recueil des travaux chimiques des Pays-Bas (*Reports of the chemical industry in the Netherlands*), 1967; E. I. Heiba et al., "oxidation by metal salts. X. One step synthesis of (gamma)-lactones from olefins," *Journal of the American Chemical Society* 1974; J. G. Stuart et al., "Cobalt-mediated alkylation of siloxy furans," Heterocycles: an international journal for reviews and communications in heterocyclic chemistry, *Japan Institute of Heterocyclic Chemistry*, 1991).

DRAWBACKS OF THE PRIOR ART

The method of Patent EP0578388 provides by fermentation a racemic mixture of dairy-lactone. The dairy-lactone obtained by fermentation requires the successive use of several fermentation species, which is a particularly important obstacle to the industrialization of the method.

The fermentation results in the production of a racemic mixture of dairy-lactone. However, it is well known that two enantiomers of the same chemical formula can have radically different properties.

BRIEF SUMMARY

Solutions Provided by the Disclosure

To remedy these drawbacks, this disclosure provides in its most general sense a method for preparing a single isomer of dairy-lactone comprising a preparation step for a glycidyl ester followed by an epoxide opening step.

The glycidyl ester has the formula (V) below, wherein $R_1$ is an alkyl group, in particular, a $CH_3$ or $C_2H_5$ group, and wherein, the dotted line represents a single or double carbon-carbon bond (of Z or E configuration):

The glycidyl ester is prepared from a lactone of formula (III) below only of R or S conformation, wherein the dotted line represents a single or double carbon-carbon bond, so that the glycidyl ester and the precursor are in pure isomeric form of only R or S conformation, and the dairy-lactone is a pure isomer of only R or S corresponding form.

Unlike the method of the prior art, the method of this disclosure provides pure enantiomers of each of the precursors of dairy-lactone and also a pure enantiomer of dairy-lactone. The method according to the disclosure preferably provides synthesizing the (Z)-dairy-lactone, of the formula $C_{12}H_{20}O_2$ and of developed formula (VIII) below.

The method according to the disclosure quickly provides, and at minimum cost, a pure solution of dairy-lactone. Preferably, a pure solution of Z-dairy-lactone is provided by the method according to the disclosure.

The synthesis step of a glycidyl ester comprises opening of the lactone and the concerted elimination of an activated alcohol from a molecule of formula (IV) below, wherein $R_2$ is chosen from the tosyl (Ts) or mesyl (Ms) groups and wherein the dotted line represents a single or double carbon-carbon bond.

(IV)

This molecule of formula (IV) is, for example, (S)-(5-oxotetrahydrofuran-2-yl)methyl-4-methylbenzenesulfonate in the case in which $R_2$ is a tosyl group, and in which the carbon-carbon bond represented by the dotted line is a single bond; or (S)-(5-oxotetrahydrofuran-2-yl)-methyl methanesulfonate in the case in which $R_2$ is a mesyl group, and in which the carbon-carbon bond represented by the dotted line is a single bond.

The molecule of formula (IV) is obtained by activation of the alcohol by sulfonation of a molecule of formula (III) below, wherein the dotted line represents a single or double carbon-carbon bond:

(III)

Sulfonation enables activation of the alcohol in order to replace it later. This sulfonation is carried out by tosylation or by mesylation.

Another alternative for the synthesis step of a glycidyl ester comprises opening of the lactone and concerted elimination of a halide of a molecule of formula (IV-bis) below, wherein X is selected from Br, Cl or I, and wherein the dotted line is a single or double carbon-carbon bond.

(IV-bis)

The molecule of formula (IV-bis) is obtained by the substitution by a halogen of the alcohol of a molecule of formula (III) wherein the dotted line represents a single or double carbon-carbon bond.

In one embodiment, the molecule of formula (IV) is obtained by activation of the alcohol by sulfonating a lactone.

Alternatively, the molecule of formula (III) in which the dotted line represents a single carbon-carbon bond is obtained by hydrogenating an α,β-unsaturated lactone.

The α,β-unsaturated lactone is preferably a lactone of formula (II) below:

(II)

This lactone is preferably the (S)-furanone (HFO) obtained by modifying the levoglucogenone from the transformation of the cellulose according to the method described in Patent Application Serial No. FR1453957 whose content is hereby incorporated herein by this reference.

Alternatively, the molecule of formula (III), in which the dotted line represents a single carbon-carbon bond, is obtained by oxidation of the dihydrolevoglucosenone in the presence of a peracid, for example, peracetic acid or MCPBA, followed by an acid or base hydrolysis of the resulting product mixture, for example, in the presence of an acid resin. This dihydrolevoglucosenone is obtained by hydrogenation of a levoglucosenone.

Advantageously, the method for preparing at least one isomer of dairy-lactone further comprises a step of lactonization of a molecule of formula (VI) below, wherein $R_3$ is preferably an alkyl group, for example, a $CH_3$ or $C_2H_5$ group, and wherein the dotted line represents a single or double carbon-carbon bond.

(VI)

This compound of formula (VI) is obtained by epoxide opening of a glycidyl ester of formula (V) described above.

Lactonization of the molecule of formula (VI) can be achieved in acidic or basic medium. Preferably, it is carried out by acid hydrolysis. This lactonization provides a molecule of formula (VII) in which the dotted line represents a single or double carbon-carbon bond.

(VII)

The molecule of formula (VII) in which the dotted line represents a single carbon-carbon bond is, for example, (S)-5-(oct-2yn-1-yl)-dihydrofuran-2(3H)-one. The molecule of formula (VII) in which the dotted line represents a double carbon-carbon bond is, for example, (R)-5-(oct-2-yn-1-yl)-furan-2(5H)-one.

The method of preparation of at least one isomer of dairy-lactone further comprises a step of syn-hydrogenation of a molecule of formula (VII).

This syn-hydrogenation of the molecule of formula (VII) leads to the synthesis of the end product, the dairy-lactone having particularly advantageous organoleptic properties. It is understood that all of the above steps lead to the synthesis of a single isomer of dairy-lactone.

According to one alternative, the synthesis of dairy-lactone from the molecule of the formula (VII) having a double bond in the ring involves a syn-hydrogenation allowing, in a single step, the reduction of the alkyne to alkene of Z configuration and the unsaturation of the lactone, α,β-unsaturated.

Alternatively, the form E enantiomer of dairy-lactone is obtained by hydrogenation.

According to one embodiment, the method of preparation of a single isomer of dairy-lactone comprises the previously listed steps.

The dairy-lactone obtained is a pure enantiomer of all possible conformations. The isomer of dairy-lactone obtained by the method is pure and of Z-R, Z-S, E-R or E-S form. Preferably, the dairy-lactone obtained is the Z-dairy-lactone. Even more preferably, the dairy-lactone obtained by the method is (Z,S)-dairy-lactone of formula (VIII) below:

(VIII)

This (Z,S)-dairy-lactone of formula (VIII) has particularly interesting organoleptic properties for use as a flavor and/or aroma in the food industry, pharmaceutics, cosmetics and perfumeries.

In one aspect, the disclosure provides a glycidyl ester of formula (V) described above, wherein $R_2$ is an alkyl group, to synthesize a pure isomer of precursor of dairy-lactone and/or a pure isomer of dairy-lactone.

According to yet another aspect, the disclosure provides the use of a pure isomer of dairy-lactone as food flavoring. Preferably, the disclosure provides the use of a pure isomer of dairy-lactone obtained by the method of this disclosure as a food flavoring. According to one embodiment, the disclosure provides the use of a pure enantiomer of (Z,S)-dairy-lactone as a food flavoring.

In another aspect, the disclosure provides the use of a pure isomer of dairy-lactone as an odorant molecule to flavor a food product. According to one embodiment, the disclosure provides the use of a pure enantiomer of (Z,S)-dairy-lactone as an odorant molecule to flavor a food product.

In another aspect, the disclosure provides the use of a pure isomer of dairy-lactone as an odorant molecule to flavor a cosmetic product. According to one embodiment, the disclosure provides the use of a pure enantiomer of (Z,S)-dairy-lactone as an odorant molecule to flavor a cosmetic product.

Advantageously, the disclosure provides a bakery product comprising a pure isomer of dairy-lactone to give a "buttered" flavor to the bakery product. In a particular embodiment, the bakery product has a pure enantiomer of (Z,S)-dairy-lactone to give a "buttered" flavor to the bakery product.

Advantageously, the bakery product contains 5 ppm to 10 ppm of (Z,S)-dairy-lactone.

Advantageously, the disclosure provides a product based on vegetable milk or animal milk substitute with a pure isomer of dairy-lactone to give a "milky" flavor to the product. In a particular embodiment, the product based on vegetable milk or animal milk substitute comprises a pure isomer of (Z,S)-dairy-lactone to give a "milky" flavor to the product.

BRIEF DESCRIPTION OF THE DRAWINGS

The disclosure will be better understood in light of non-limiting examples of the embodiment.

DETAILED DESCRIPTION

Example 1

Synthesis of (S)-furanone (HFO) of Formula (II) from a Specific Ketone, Levoglucosenone Any of the methods described in Patent Application Serial No. FR1453957 whose content is incorporated herein by this reference may be used.

(S)-furanone or (S)-4-hydroxymethylbutenolide has the formula (II) below:

(II)

4-hydroxymethylbutenolide of formula (II) is prepared from levoglucosenone (LGO), which is obtained by use of biomass, according to the particular implementation of the "one-pot" method.

Oxidation

In a reactor, an aqueous solution of hydrogen peroxide $H_2O_2$ at 30% (2.57 mmol, 0.26 mL, 1.2 eq. relative to the LGO) is added in one portion to an LGO suspension (270 mg, 2.14 mmol) and CAL-B lipase (NOVOZYM® 435, 75 mg, 315 U/nmol LGO) in ethyl acetate (3 mL) with stirring at room temperature in a planar agitation incubator. For this example, as for all the examples described below, 1 g of NOVOZYM® 435 corresponds to 9000 units of CAL-B lipase (activity measured after residence of the enzyme in ethyl acetate). The reaction mixture is stirred at 40° C. for 4 hours then evaporated to dryness.

Acid Hydrolysis

Concentrated hydrochloric acid (5 mmol, 0.4 mL) is added to a solution of this crude mixture in methanol (5 mL) at room temperature. The reaction mixture is heated under stirring for 8 to 16 hours, so as to convert the formate to the corresponding alcohol. The reaction mixture is evaporated to dryness with a silica gel. The crude product is purified by chromatography on silica gel (elution with 75%-100% ethyl acetate in cyclohexane) to obtain pure (S)-4-hydroxymethylbutenolide of formula (II) (175 mg, 72%).

$^1$H NMR (CDCl$_3$): d 7.53 (dd, J=1.5 and 5.7 Hz, 1 H), 6.2 (dd, J=1.5 and 5.7 Hz, 1 H), 5.17 (m, 1 H), 4.0 (d, J=3.6 and 12.0 Hz, 1 H), 3.80 (dd, J=3.6 and 12.0 Hz, 1 H)

$^{13}$C NMR (CDCl$_3$): d 173.5 (s), 154.0 (d), 122.8 (d), 84.3 (d), 62.2 (t)

Alternatively, after of the LGO treatment step with the lipase, the latter is separated from the reaction medium before the dry evaporation step of the medium. The acid hydrolysis is then carried out as described above. Pure 4-hydroxymethylbutenolide is also obtained, with the same yield of 72%.

In other variants of the method, the acid hydrolysis step is carried out directly on the reaction medium obtained after the oxidation step, without having previously performed an evaporation to dryness step. Whether or not the lipase is removed from the reaction medium by filtration, in such embodiments, the reaction yield is similar to that obtained for the implementation mode described above in detail, that is, about 72%.

Example 2

Synthesis of 4-hydroxymethylbutyrolactone of Formula (III) from (S)-furanone of Formula (II)

(S)-4-hydroxymethylbutenolide or (S)-furanone of formula (II) obtained in Example 1 is subjected to catalytic hydrogenation, in the following manner.

Pd/C (10% p/p, 250 mg) is added to a 4-hydroxymethyl-butenolide solution (1.4 g, 12.3 mmol) in ethyl acetate (15 mL) at room temperature. The stirring suspension is degassed three times under nitrogen/vacuum. A hydrogen atmosphere at room temperature then hydrogenates the suspension for 4 hours. The crude mixture is filtered through a celite buffer and the filtrate is concentrated to dryness with a silica gel. The crude product is purified by chromatography on silica gel (elution with a gradient from 75% to 100% ethyl acetate in cyclohexane) to give a pure (S)-4-hydroxymethylbutyrolactone of formula (III) (1.19 g, 82%).

$^1$H NMR (CDCl$_3$): d 4.64 (m, 1 H), 3.92 (dd, J=2.7 and 12.6 Hz, 1 H), 3.66 (dd, J=4.5 and 12.6 Hz, 1 H), 2.72-2.49 (m, 3 H), 2.35 to 2.09 (m, 2 H)

$^{13}$C NMR (CDCl$_3$): d 177.7 (s), 80.8 (d), 64.1 (t), 28.7 (t), 23.1 (t)

This synthetic route provides with high yields, the (S)-4-hydroxymethylbutyrolactone of formula (III) and S form, whose structure is confirmed by proton and carbon NMR, and polarimetry (optical rotation).

Example 2bis

Figure 1:
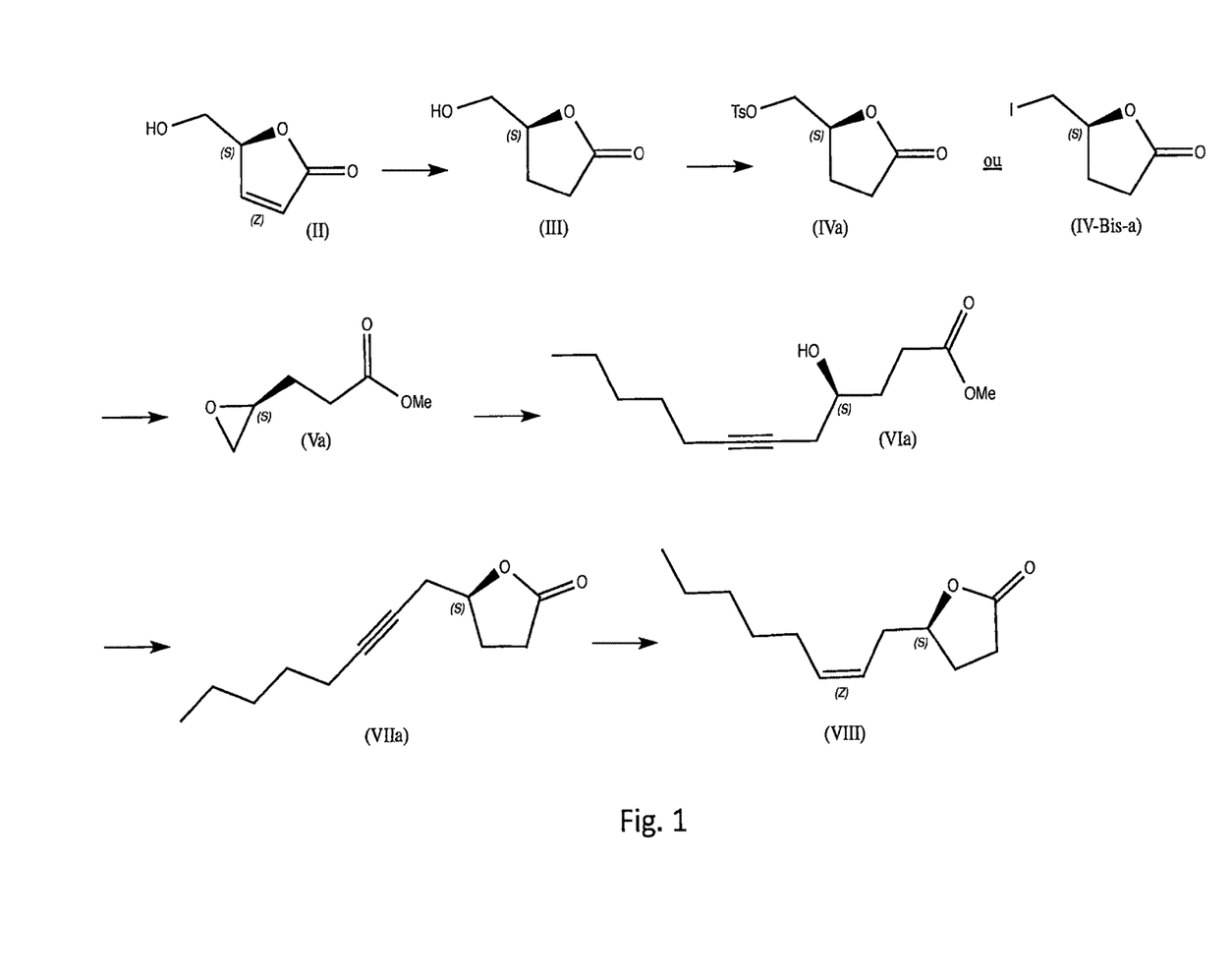
FIG. 1 is a diagram of the various steps of the synthesis method of at least one precursor of an isomer of (Z,S)-dairy-lactone and an isomer of (Z,S)-dairy-lactone from the lactone (II).
Figure 2:
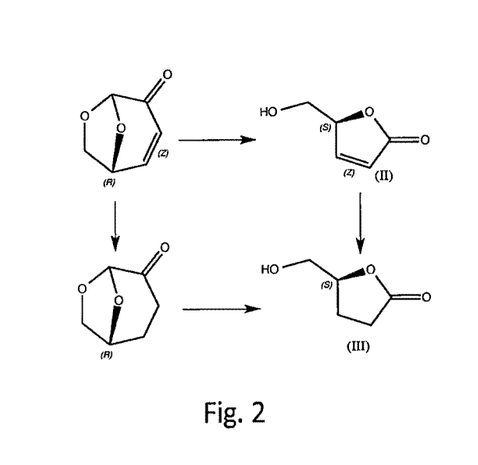
FIG. 2 is a diagram of the enzymatic synthesis of precursors of the dairy-lactone, (S)-furanone (molecule II) and of 4-hydroxymethylbutyrolactone (molecule III) and is described in Examples 1 and 2.
Figure 3:
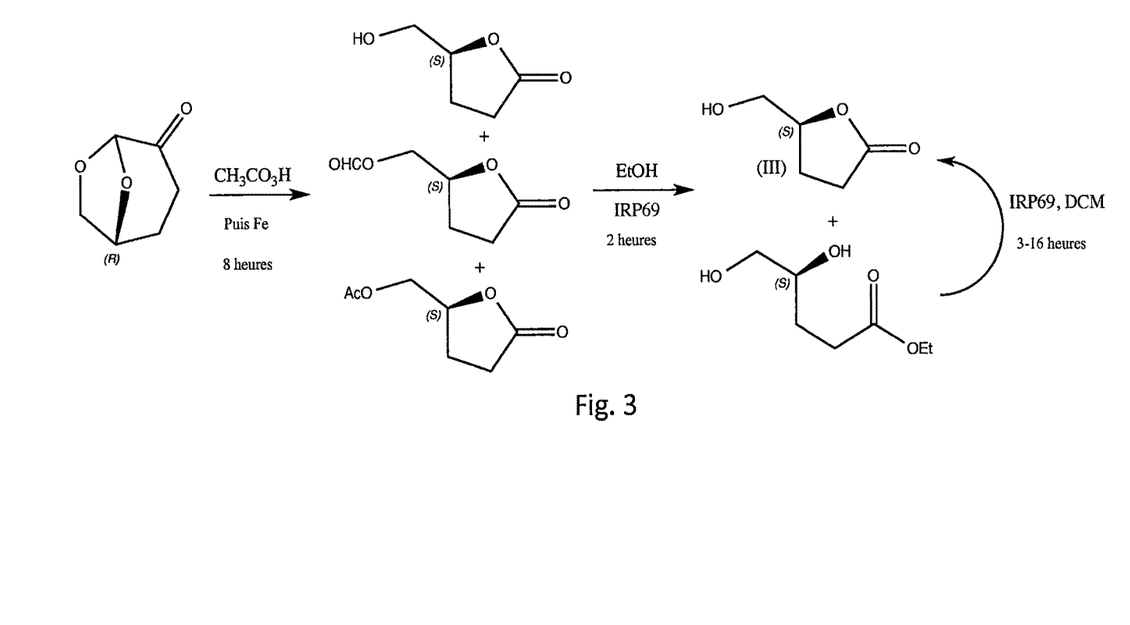
FIG. 3 depicts an alternative synthesis route of 4-hydroxymethylbutyrolactone (molecule III) by chemical synthesis and is described in Example 2bis.
Figure 4:
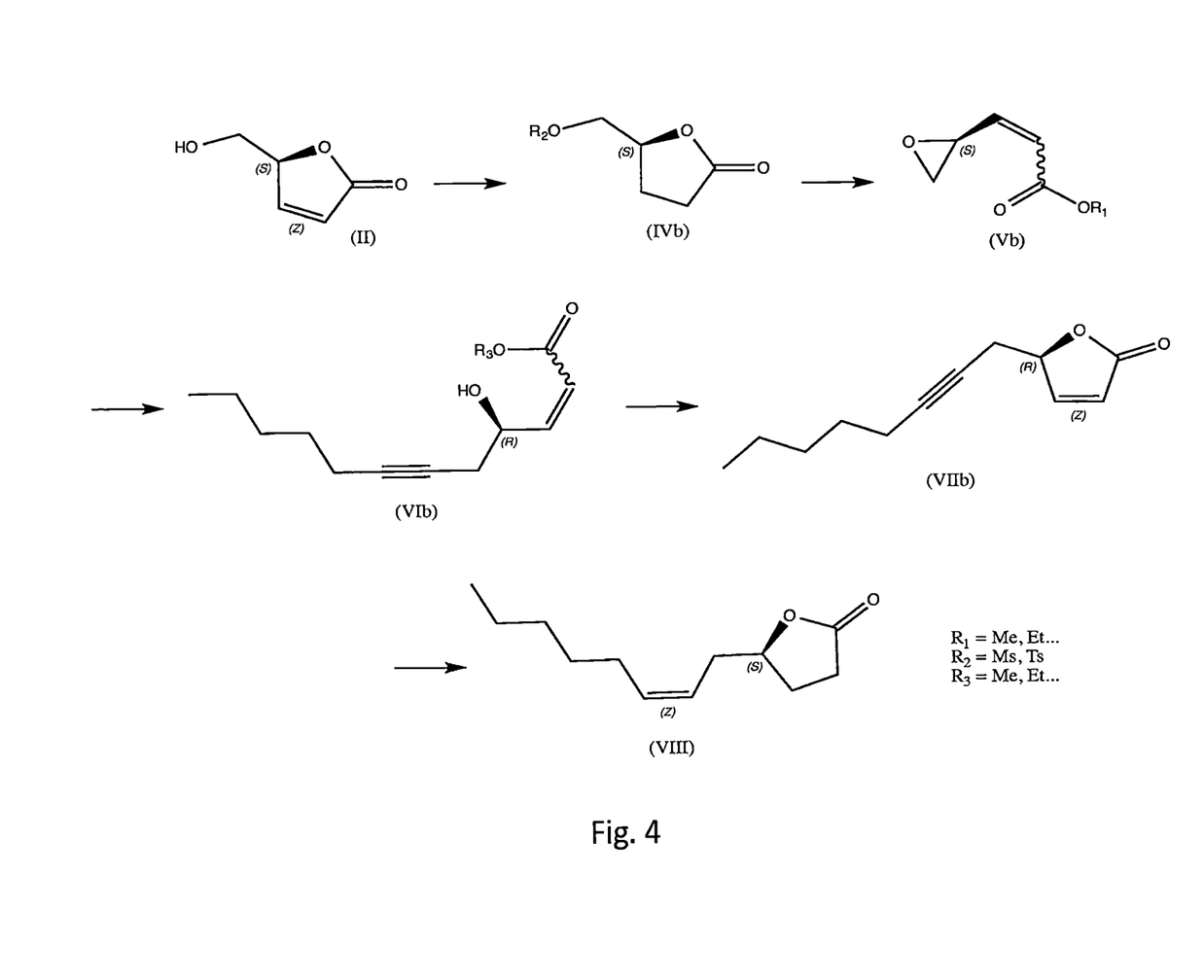
FIG. 4 depicts an alternative synthesis route of at least one precursor of an isomer of (Z,S)-dairy-lactone and an isomer of the (Z,S)-dairy-lactone.

Synthesis of (S)-4-hydroxymethylbutyrolactone of Formula (III) from dihydrolevoglucosenone This example is an alternative to Examples 1 and 2 above and is presented in FIG. 3.

(S)(+)-5-(Hydroxymethyl)dihydrofuran-2(3H)-one (III)

To a dihydrolevoglucosenone solution (5.0 g, 39 mmol) in water (30 mL) is added 32% peracetic acid (13 g, 55 mmol) over a period of 30 minutes while maintaining the mixture temperature between 25° C. and 35° C. The mixture is stirred at this temperature for 8 hours, then is neutralized by pouring it on the iron dust (1.0 g) and by stirring until no peroxides (iodine test paper, 5 minutes) and then for an additional 16-hour period. The mixture is then filtered through celite and concentrated under reduced pressure to give an oil-solid mixture. The latter is then suspended in ethyl acetate (50 mL) and filtered to remove the iron salts, which are then washed with ethyl acetate. The organic phases are then combined and concentrated under reduced pressure to provide a colorless oil (4.23 g, 80%, mixture of lactone III, its formate and its acetate). This oil is then taken up in ethanol (40 mL) and is then added IRP-69 (H+) (600 mg), and the mixture is refluxed for 1 hour before being cooled to ambient temperature. The ethanol is evaporated under reduced pressure and the residue is re-dissolved in dichloromethane (10 mL) and stirred for 16 hours. The mixture is then filtered and concentrated under reduced pressure to give (S)-4-hydroxymethylbutyrolactone as a colorless oil (75%).

Example 3

Synthesis of (S)-(5-oxotetrahydrofuran-2-yl)methyl 4-methylbenzenesulfonate of Formula (IVa) from 4-hydroxymethylbutyrolactone of Formula (III)

Tosyl chloride (1.55 g, 8.1 mmol) is added in one portion to a solution constituted by a mixture of 4-hydroxymethyl-butyrolactone (0.9 g, 7.7 mmol) in DCM (5 mL)/pyridine (1.5 mL) at room temperature under nitrogen. The reaction mixture is stirred at room temperature for 4 hours. DCM (20 mL) is added and the reaction mixture is rinsed with a solution of HCl 3M, brine, dried over anhydrous magnesium sulfate, filtered and concentrated to obtain a dry product. This crude product is then triturated with diethyl ether (15 mL). The generated white precipitate is recovered by filtration and dried to obtain a pure product of (S)-(5-oxotetra-hydrofuran-2-yl)methyl 4-methylbenzenesulfonate formula (IVa) (1.3 g, 62%), which is then used as is, without further purification for the following synthesis.

$^1$H NMR (500 MHz): 7.8 ppm (2 H, d); 7.4 ppm (2 H, d); 4.7 ppm (1 H, m); 4.2 ppm (2 H, m); 2.6 ppm (2 H, m); 2.5 ppm (3 H, s); 2.4 ppm (1 H, m); 2.1 ppm (1 H, m)

Example 4

Synthesis of (S)-5-(iodomethyl)dihydrofuran-2(3H)-one (IV-bis-a)

Triphenylphosphine (524 mg, 2 mmol) is added to a 4-hydroxymethylbutyrolactone solution (116 mg, 1 mmol), iodine (508 mg, 2 mmol) and imidazole (136 mg, 2 mmol) in acetonitrile (10 mL) at 0° C. The mixture is then refluxed overnight before being cooled to room temperature and then extracted with ether (3×20 mL). The organic phases are then combined, washed with water (20 mL), brine (20 mL) then dried over anhydrous magnesium sulfate. After filtration and concentration under reduced pressure, the crude product is purified by flash chromatography (3:1 hexane:ethyl acetate) on silica gel to give, after combination and evaporation of the pure fractions, the product of formula (IV-bis-a) as a colorless oil (160 mg, 71%).

Example 5

Synthesis of Glycidyl ester of Formula (Va) from the (S)-(5-oxotetrahydrofuran-2-yl) methyl 4-methylbenzenesulfonate of Formula (IVa)

Sodium methoxide (0.7 g, 13 mmol) is added in one portion to a mixture of (S)-(5-oxotetrahydrofuran-2-yl) methyl 4-methylbenzenesulfonate of formula (IVa) tosylated (3 g, 11 mmol) in methanol (20 mL) at 0° C. under nitrogen. The reaction mixture is stirred at room temperature for one hour. Ethyl acetate (100 mL) is added and the reaction mixture is quenched with a saturated aqueous solution of ammonium chloride (50 mL). The phases are separated and the aqueous phase is again extracted with ethyl acetate. The combined organic phases are washed with brine, then dried over anhydrous magnesium sulfate, filtered and concentrated by drying to obtain a glycidyl ester epoxide (0.9 g, 63%) as an oil. This crude product is used as is to synthesize the following desired product.

$^1$H NMR (500 MHz): 3.7 ppm (3 H, s); 3.0 ppm (1 H, m); 2.78 ppm (1 H, t) ppm 2.52 (1 H, dd); 2.48 ppm (2 H, t) 2.0 ppm (H, m) 1.8 ppm (1 H, m)

Example 6

Synthesis of Glycidyl ester of Formula (Va) from the (S)-5-(iodomethyl)dihydrofuran-2(3H)-one (IV-bis-a)

Sodium methoxide (0.7 g, 13 mmol) is added in one portion to a mixture of (S)-5-(iodomethyl)dihydrofuran-2 (3H)-one (IV-bis-a) (2.5 g, 11 mmol) in methanol (20 mL) at 0° C. under nitrogen. The reaction mixture is stirred at room temperature for one hour. Ethyl acetate (100 mL) is added and the reaction mixture is quenched with a saturated aqueous solution of ammonium chloride (50 mL). The phases are separated and the aqueous phase is again extracted with ethyl acetate. The combined organic phases are washed with brine, then dried over anhydrous magnesium sulfate, filtered and concentrated by drying to obtain an epoxide glycidyl ester (0.9 g, 63%) as an oil. This crude product is used as is to synthesize the following desired product.

$^1$H NMR (500 MHz): 3.7 ppm (3 H, s); 3.0 ppm (1 H, m); 2.78 ppm (1 H, t) 2.52 ppm (1 H, dd); 2.48 ppm (2 H, t) 2.0 ppm (1 H, m) 1.8 ppm (1 H, m)

Example 7

Synthesis of methyl (S)-4-hydroxyundec-5-ynoate of Formula (Via) from glycidyl ester of Formula (Va)

N-BuLi (2.5 mol/L in hexane, 3 mL, 8.3 mmol) is added to a mixture of hept-1-yne (750 mg, 7.8 mmol) in dry THF (10 mL) at −78° C. under nitrogen. The reaction mixture is mixed at the same temperature for 20 minutes. BF$_3$Et$_2$O (1 mL, 8.3 mmol) is then added at −78° C. The reaction is continued at the same temperature for 20 minutes before incorporating the previously obtained pure glycidyl ester epoxide (1 g, 7.7 mmol). The reaction is continued for 2 hours at −78° C. The reaction mixture, back to −10° C., is then quenched with a saturated aqueous solution of ammonium chloride (10 mL) and extracted with ethyl acetate (3×30 mL).

The combined organic phases are washed with brine, dried over anhydrous magnesium sulfate, filtered and concentrated by drying. The crude product (absorbed on celite) is purified by flash chromatography (5% to 30% of EtOAc with cyclohexane as eluent) on silica gel to give, after combination and evaporation of the pure fractions, the PRODUCT 6 (700 mg, 40%) as a colorless oil.

Example 8

Synthesis of (S)-5-(oct-2-yn-1-yl)dihydrofuran-2 (3H)-one of Formula (VIIa) from methyl (S)-4-hydroxyundec-5-ynoate of Formula (VIa)

A mixture of methyl (S)-4-hydroxyundec-5-ynoate of formula (VIa) (600 mg, 2.6 mmol) in 5 mL of an aqueous solution of 80% acetic acid is heated with stirring at 50° C. for 18 hours. Ethyl acetate (20 mL) is added and the reaction mixture is rinsed with sodium bicarbonate-saturated aqueous solution, brine, then dried over anhydrous magnesium sulfate, filtered and then concentrated by drying. The crude product (absorbed on celite) is purified by flash chromatography (5% to 30% of EtOAc with cyclohexane as eluent) on silica gel to give, after combination and evaporation of the pure fractions, a lactone called (S)-5-(oct-2-yn-1-yl)dihydrofuran-2(3H)-one of formula (VIIa) (275 mg, 53%) as a colorless oil.

Example 9

Synthesis of (Z,S)-dairy-lactone from (S)-5-(oct-2-yn-1-yl)dihydrofuran-2(3H)-one of Formula (VIIa)

A mixture of (S)-5-(oct-2-yn-1-yl)dihydrofuran-2(3H)-one of formula (VIIa) (270 mg, 1.39 mmol) in 10 mL of ethyl acetate is hydrogenated in a stream of dihydrogen stirred with Lindlar catalyst (50 mg) at room temperature for 6 hours. The reaction mixture is filtered through a celite filter and concentrated by drying to obtain the pure (Z)-dairy-lactone (270 mg, 90%) as a colorless oil. The obtained dairy-lactone is of the Z-S form.

$^1$H NMR (500 MHz): 5.6 ppm (1 H, m); 5.35 ppm (1 H, m); 2.55 ppm (3 H, m); 2.4 ppm (1 H, m); 2.3 ppm (1 H, m); 2.05 ppm (2 H, m); 1.9 ppm (1 H, m); 1.2-1.4 ppm (7 H, m), 0.9 ppm (3 H, t)

The invention claimed is:

1. A method for preparing a precursor molecule of formula (VI) of a single isomer of dairy-lactone, wherein R$_1$ and R$_3$ are alkyl groups and wherein the dashed lines represent a single or double carbon-carbon bond, the method comprising:

preparing a glycidyl ester of formula (V) as a pure isomeric form only of R or S conformation, the glycidyl ester, of formula (V) having an epoxide group, said preparation of the glycidyl ester of formula (V) followed by opening the epoxide group of the glycidyl ester of formula (V) in the presence of hept-1-yne so as to form the molecule of formula (VI); wherein the glycidyl ester of formula (V) and the molecule of formal (VI) follows:

2. The method according to claim 1, wherein the glycidyl ester of formula (V) is prepared from a lactone of formula (III) only of R or S conformation by a method comprising opening the lactone of formula (III), where the dashed line of the lactone of formula (III) represents a single or double carbon-carbon bond, so that said glycidyl ester and said precursor molecule of formula (VI) are in pure isomeric form only of R or S form, and that the dairy-lactone is a pure isomer only of R or S corresponding form:

3. The method according to claim 2, wherein preparing said glycidyl ester consists of opening the lactone in molecule of formula (IV) and concerted elimination of an activated alcohol from a molecule of formula (IV), wherein $R_2$ is selected from the group consisting of a tosyl group and a mesyl group, and wherein the dashed line of the molecule of formula (IV) represents a single or double carbon-carbon bond, wherein said molecule of formula (IV) is obtained by a process comprising activation of the alcohol of the lactone of formula (III):

4. The method according to claim 2, wherein preparing said glycidyl ester consists of opening the lactone of formula (III) and concerted elimination of a halide of a molecule of formula (IV-BIS), wherein X is selected from the group consisting of Br, Cl, and I, and wherein the dashed line of the molecule of formula (IV-BIS) represents a single or double carbon-carbon bond, said molecule of formula (IV-BIS) being obtained by substituting halogen for the alcohol group in a lactone of formula (III):

5. The method according to claim 3, wherein said molecule of formula (IV) is obtained by activating the alcohol group of a molecule of formula (III) by sulfonation.

6. The method according to claim 5, wherein the dashed line of said molecule of formula (III) represents a single carbon-carbon bond obtained by hydrogenating an α,β-unsaturated lactone.

7. The method according to claim 5, wherein said molecule of formula (III) is obtained by oxidizing a dihydrolevoglucosenone in the presence of a peracid, followed by hydrolysis, said dihydrolevoglucosenone being obtained by hydrogenating a levoglucosenone.

8. The method according to claim 1, wherein the method further comprises lactonizing the molecule of formula (VI) to obtain a molecule of formula (VII), wherein the dashed line of formula (VII) represents a single or double carbon-carbon bond:

9. The method according to claim 1, further comprising:
incorporating a pure isomer of dairy-lactone obtained thereby into a food.

10. The method according to claim 1, further comprising:
incorporating a pure isomer of dairy-lactone obtained thereby into a cosmetic product.

11. The method according to claim 9, wherein the food is a bakery product.

12. The method according to claim 9, wherein the food is a vegetable milk or animal milk substitute.

13. The method according to claim 1, wherein $R_1$ and $R_3$ are each independently selected from $CH_3$ and $C_2H_5$.

14. A method for preparing a single isomer of dairy-lactone of formula (VIII), the method comprising the steps of:
preparing a glycidyl ester of formula (V) having an epoxide group as a pure isomeric form only of R or S conformation, followed by opening of the epoxide group to obtain a molecule of formula (VI), a lactonization step of the molecule of formula (VI), wherein the dashed line thereof represents a single or double carbon-carbon bond to obtain a molecule of formula (VII), and a syn-hydrogenation step of the molecule of formula (VII) to form the single isomer of dairy-lactone of formula (VIII), wherein $R_1$ and $R_3$ are alkyl groups, and wherein the dashed lines represent a single or double carbon-carbon bond, and wherein the molecules of formula (V), (VI), (VII), and (VIII) have the following structures:

(VIII)

15. The method according to claim 14, wherein $R_1$ and $R_3$ are each independently selected from $CH_3$ and $C_2H_5$.

* * * * *

UNITED STATES PATENT AND TRADEMARK OFFICE
CERTIFICATE OF CORRECTION

PATENT NO. : 10,183,923 B2  
APPLICATION NO. : 15/565287  
DATED : January 22, 2019  
INVENTOR(S) : Florent Allais et al.

Page 1 of 1

It is certified that error appears in the above-identified patent and that said Letters Patent is hereby corrected as shown below:

In the Claims

Claim 1, Column 10, Line 45, change "formal (VI) follows:" to --formula (VI) are as follows:--

Signed and Sealed this  
Twelfth Day of March, 2019

Andrei Iancu  
*Director of the United States Patent and Trademark Office*